US006444697B2

(12) United States Patent
Wright et al.

(10) Patent No.: US 6,444,697 B2
(45) Date of Patent: *Sep. 3, 2002

(54) SYNTHETIC COMPOUNDS FOR TREATMENT OF INFLAMMATION

(75) Inventors: Amy E. Wright, Fort Pierce, FL (US); Ralph-Heiko Mattern, San Diego; Robert S. Jacobs, Santa Barbara, both of CA (US)

(73) Assignees: Harbor Branch Oceanographic Instutition, Inc., Fort Pierce, FL (US); Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/916,470

(22) Filed: Jul. 27, 2001

Related U.S. Application Data

(63) Continuation of application No. 09/349,316, filed on Jul. 8, 1999
(60) Provisional application No. 60/091,991, filed on Jul. 8, 1998.

(51) Int. Cl.⁷ .................. A61K 31/40; A61K 31/405
(52) U.S. Cl. .................. 514/408; 514/414; 514/415; 514/416; 514/417; 514/419
(58) Field of Search ................ 514/414, 408, 514/415, 416, 417, 419

(56) References Cited

U.S. PATENT DOCUMENTS

| | | | |
|---|---|---|---|
| 4,866,084 A | | 9/1989 | Gunasekera et al. |
| 4,970,226 A | | 11/1990 | Sun et al. |
| 5,290,777 A | | 3/1994 | McConnell et al. |
| 5,464,835 A | | 11/1995 | McConnell et al. |
| 5,496,950 A | | 3/1996 | McConnell et al. |
| 5,955,462 A | * | 9/1999 | Jacobs et al. ............... 514/254 |
| 6,323,233 B1 | * | 11/2001 | Wright et al. ............... 514/408 |

FOREIGN PATENT DOCUMENTS

| | | |
|---|---|---|
| EP | 0 397 060 A2 | 11/1990 |
| EP | 0 470 490 A1 | 2/1992 |
| EP | 0 887 348 A1 | 12/1998 |
| FR | 1403617 | 5/1965 |
| WO | WO 98/18466 | 5/1988 |
| WO | WO 94/19343 | 9/1994 |

\* cited by examiner

*Primary Examiner*—Theodore J. Criares
*Assistant Examiner*—Jennifer Kim
(74) *Attorney, Agent, or Firm*—Sliwanchik, Lloyd & Saliwanchik

(57) ABSTRACT

Novel uses of biologically active bis-heterocyclic e.g. bis-indole alkaloid compounds which have improved activity are disclosed. Pharmaceutical compositions containing the compounds are also disclosed. Specifically, the novel Utility pertains to the anti-immunogenic and neurogenic inflammatory properties exhibited by the bis-indole compounds and their analogs.

17 Claims, 2 Drawing Sheets

SYNTHETIC COMPOUNDS FOR TREATMENT OF INFLAMMATION

CROSS-REFERENCE TO A RELATED APPLICATION

This application is a continuation of U.S. Ser. No. 09/349,316, filed Jul. 8, 1999; which claims priority from provisional application U.S. Ser. No. 60/091,991, filed Jul. 8, 1998.

The subject invention was made with government support under a research project supported by NOAA Grant No. NA36RG0537. The government has certain rights in this invention.

FIELD OF THE INVENTION

The subject invention pertains to compounds which are useful as anti-inflammatory agents and to compositions containing such compounds as active ingredients. More particularly, the invention concerns novel uses for biologically active bis-heterocyclic compounds, e.g. bis-indoles, and to pharmaceutical compositions containing these compounds. The novel use of the compounds relates to the anti-inflammatory properties of the disclosed bis-heterocyclic compounds. Specifically exemplified herein are the compounds identified as soritin A, HB-238, Bis(3, 3'indolyl)methane, HB-236, 2-Bis(3,3'indolyl)acetaldehyde, HB-237, and their salts, analogs and derivatives.

BACKGROUND OF THE INVENTION

The prevention and control of inflammation is of prime importance to man, and much research has been devoted to development of compounds having anti-inflammatory properties. Certain methods and chemical compositions have been developed which aid in inhibiting or controlling inflammation, but additional anti-inflammatory methods and compositions are needed.

Bis-heterocyclic compounds such as bis-indoles have been previously described as having antimicrobial, antitumor or antiviral activity. Specifically, the bis-indole compounds known as topsentins are disclosed in U.S. Pat. No. 4,866,084. Dragmacidin and its related compounds isolated from the marine sponge of the Dragmacidon sp. are disclosed in U.S. Pat. No. 4,970,226. These patents are herein incorporated by reference. These compounds as well as the homocarbonyl topsentins and hamacanthins have also been described as having inhibitory activity against cellular inflammatory responses. See U.S. Pat. Nos. 5,290,777 and 5,464,835 which are also hereby incorporated by reference. The present invention provides compounds having advantageous potent anti-inflammatory activity.

Other advantages and further scope of applicability of the present invention will become apparent from the detailed descriptions given herein; it should be understood, however that the detailed descriptions, while indicating preferred embodiments of the invention, are given by way of illustration only, since various changes and modifications within the spirit and scope of the invention will become apparent from such descriptions.

BRIEF SUMMARY OF THE INVENTION

The present invention provides compounds which are useful as anti-inflammatory agents. The objects of the present invention are accomplished by the provision of a novel utility for certain bis-heterocyclic compounds.

In one example, the compounds useful according to the subject invention have the following formula:

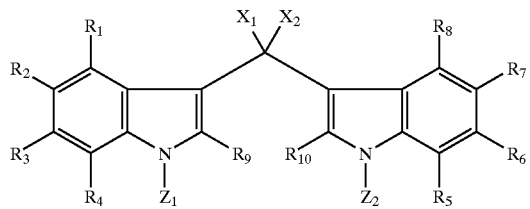

$R_{1-10}$ are the same or different selected from —H, —OH, halogen, —COOH, —COOR, C1–C8 alkyl, C1–C8 alkoxyl, mesyl, tosyl, —OCOR, or $NZ_1Z_2$ (wherein the Zs can be the same or different);

$X_1$ and $X_2$ are the same or different selected from —H, —R, —COY, $C(NZ_1)Y$ Y is —H, —OH, $NZ_1Z_2$ (wherein the $Z_1$ and $Z_2$ can be the same or different) C1–C8 alkyl, C1–C8 alkoxyl or an amino acid linked through the amine functionality forming an amide bond;

$Z_1$ and $Z_2$ are the same or different and independently selected from —H, —OH, C1–C8 alkyl, C1–C8 alkoxyl or —COR;

R is C1–C8 alkyl, or aryl

A preferred embodiment of the subject invention pertains to the bis-indole compounds soritin A, HB-238, (I), Bis(3, 3'indolyl)methane, HB-236, (II) and 2,2-Bis(3,3'indolyl)acetaldehyde, HB-237 (III).

As described herein, the invention also comprises pharmaceutical compositions, e.g. anti-inflammatory compositions, containing as an active ingredient an effective amount, preferably between about 0.1 to 45%, especially 1 to 25%, by weight based on the total weight of the composition, of one or more compounds according to the formula expressed above and a non-toxic, pharmaceutically acceptable carrier or diluent. In addition, a pharmaceutical composition can comprise at least one of the subject compounds and a second component comprising at least one other active compound. Such other active compounds include but are not limited to, anti-inflammatory compounds for example, steroidal compounds, including hydrocortisone and the like; or non-steroidal anti-inflammatories, including acetylsalicylic acid (aspirin), ibuprofen, acetaminophen, indomethacin, and the like. The second active ingredient can include antiviral, antibacterial, antifungal or other antimicrobial compounds or antitumor compounds as well.

As described herein, the invention further comprises processes for the production of compounds and compositions of the invention and novel methods of use thereof, e.g. methods of inhibition of the inflammatory response in an animal.

In accordance with the invention, methods for inhibiting inflammation comprise administering to an animal in need of such treatment an effective amount of the pharmaceutical composition.

DETAILED DISCLOSURE OF THE INVENTION

Figure 1:
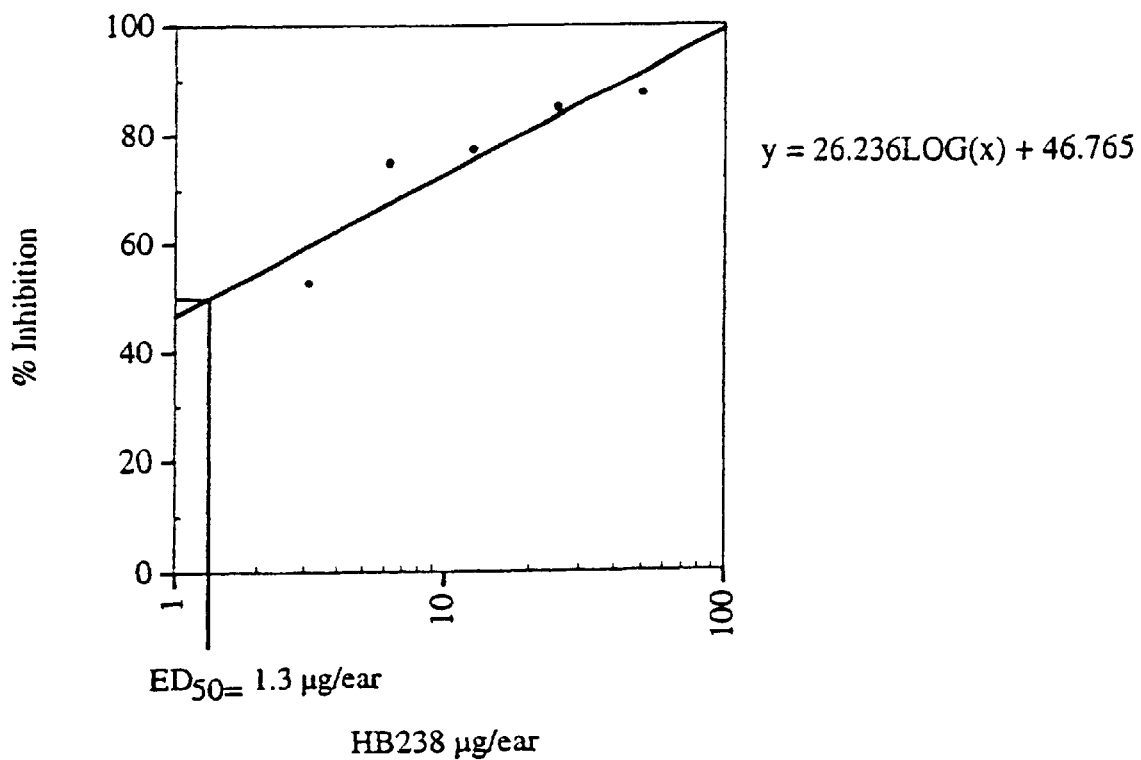
FIG. 1 shows the dose response for soritin A (HB-238) as measured by percent inhibition of edema in the PMA-induced mouse ear anti-inflammatory assay.
Figure 2:
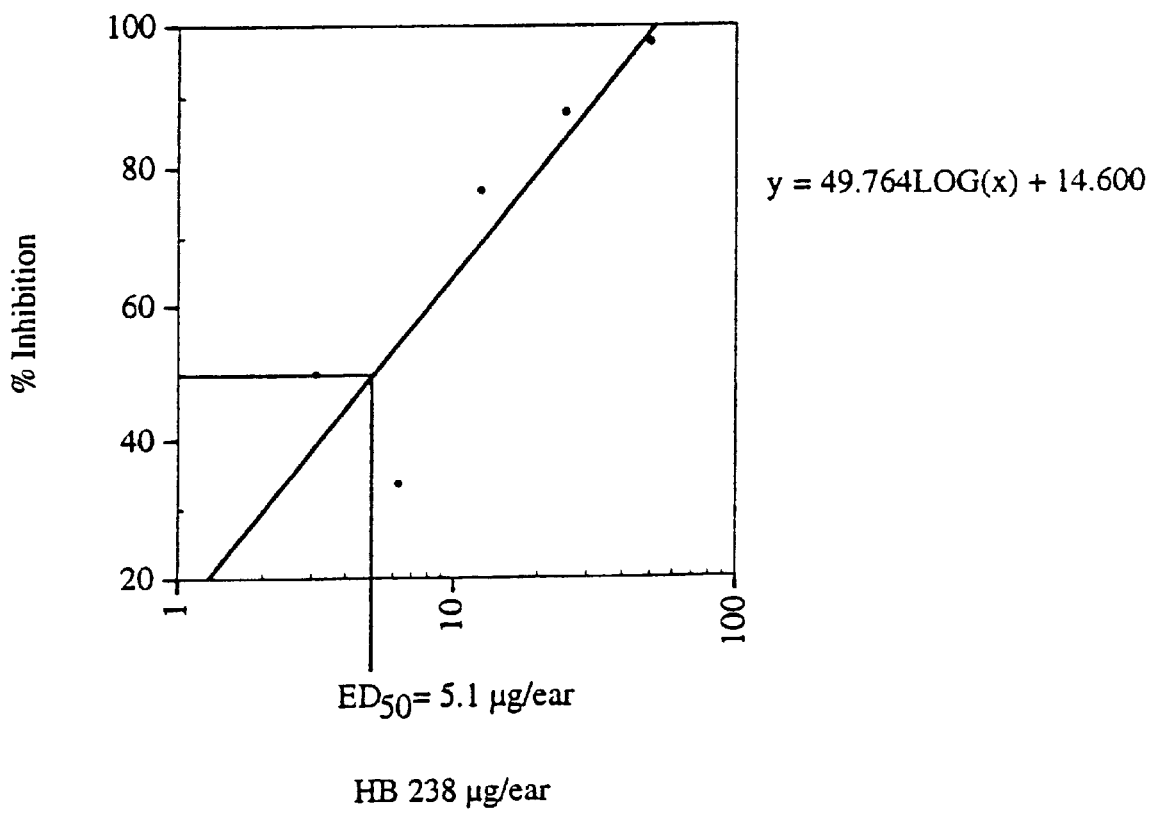
FIG. 2 shows the dose response for soritin A (HB-238) as measured by percent inhibition of edema in the RTX-induced mouse ear anti-inflammatory assay.

The subject invention pertains to a novel use as an anti-inflammatory agent of bis-heterocyclic compounds and compositions comprising the bis-heterocyclic compounds. Surprisingly, the bis-heterocycle compounds of the subject invention can be highly effective in inhibiting immunogenic and neurogenic inflammation.

In one example, compounds useful according to the subject invention have the following formula:

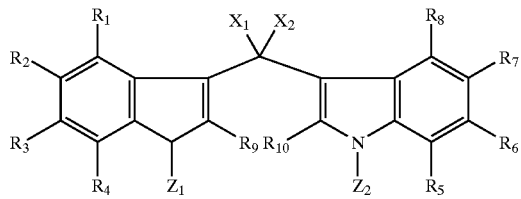

$R_{1-10}$ are the same or different selected from —H, —OH, halogen, —COOH, —COOR, C1–C8 alkyl, C1–C8 alkoxyl, mesyl, tosyl, —OCOR, or $NZ_1Z_2$ (wherein the Zs can be the same or different);

$X_1$ and $X_2$ are the same or different selected from —H, —R, —COY, C($NZ_1$)Y Y is —H, —OH, $NZ_1Z_2$ (wherein the $Z_1$ and $Z_2$ can be the same or different) C1–C8 alkyl, C1–C8 alkoxyl or an amino acid linked through the amine functionality forming an amide bond;

$Z_1$ and $Z_2$ are the same or different and independently selected from —H, —OH, C1–C8 alkyl, C1–C8 alkoxyl or —COR;

R is C1–C8 alkyl, or aryl

A preferred embodiment of the subject invention pertains to the bis-indole compounds soritin A, HB-238, (I), Bis(3, 3'indolyl)methane, HB-236, (II) and 2,2-Bis(3,3'indolyl) acetaldehyde, HB-237 (III).

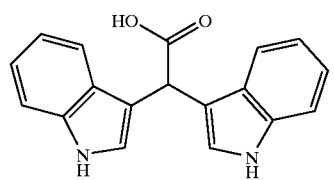
(I)

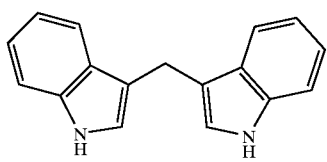
(II)

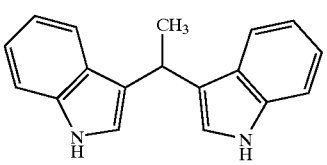
(III)

Skilled chemists having the benefit of the instant disclosure can readily use standard synthetic procedures to prepare the subject compounds. A variety of coupling procedures can be used including dimerization of indoles with aldehydes, Friedel Craft acylations, Friedel Craft alkylations and various metal mediated coupling reactions. Preparation of amino acid substituted soritin A can easily be conducted using standard peptide coupling reagents such as DCC, BOP, PyBOP, HBTU and TBTU.

A novel use for the described compounds and compositions is their administration to an animal, e.g., a human, as an agent in the control of a neurogenic or immunogenic inflammatory response. The determination that the subject compounds have inhibitory activity against immunogenic and neurogenic inflammation is unexpected and advantageous.

Anti-inflammatory activity can occur by modes of action which can include, but are not limited to, lipid-mediated inflammatory responses, e.g., (i) suppression of cellular activation of phospholipase A2, either directly (as is known for the anti-inflammatory compound, manoalide) or indirectly (as is known for the anti-inflammatory compound, hydrocortisone); (ii) by inhibiting, or controlling, cyclooxygenation of arachidonic acid, similar to the action of non-steroidal anti-inflammatory drugs; or (iii) by affecting lipooxygenase products of peroxidase reactions to arachidonic acid, or by non-lipid-mediated inflammatory responses, e.g., protease-induced inflammatory responses, and the like.

The compounds and compositions of the subject invention advantageously can block the immunogenic inflammatory pathway, thereby providing a method for inhibiting immunogenic inflammation. Accordingly, the subject compounds and compositions can be useful in the treatment of acute allergic response, asthma, rheumatoid arthritis, osteoarthritis and other inflammatory conditions involving acute and/or chronic joint inflammation. Neurogenic inflammation is evoked by neuropeptides released from primary afferent nerve terminals and by other secondarily released inflammatory mediators. Specifically, neurogenic inflammation can be evoked by neuropeptides, such as substance P (SP), calcitonin gene-related peptide (CGRP), vasoactive intestinal peptide (VIP), and neurokinin A (NKA), released from primary afferent C-fiber nerve terminals and histamine, secondarily released from mast cells (Dray, A. [1992] "Neuro pharmacological mechanisms of capsaicin and related substances" *Biochem Pharm* 44(4):611–15).

It is known that capsaicin (CAP), the active constituent found in cayenne pepper, induces an acute neurogenic inflammatory response when applied topically to skin. CAP is a highly selective pain producing substance that selectively stimulates nociceptive and thermal-sensitive nerve endings in tissues by acting on a specific membrane receptor. The mode of action of capsaicin therefore differs significantly from phorbol myristate acetate (PMA)-induced inflammation. By comparison, PMA elicits its pro-inflammatory effects through cellular activation of specific immune cells, such as macrophages and neutrophils. Consequently, the pain response to PMA develops more slowly than the immediate, but transient, pain response to capsaicin.

The compounds and compositions of the subject invention advantageously can block the nociceptive (CAP-induced) inflammatory pathway, thereby providing a method for inhibiting neurogenic inflammation. Accordingly, the subject compounds and compositions can be useful in the treatment of chronic pain, migraines, thermal-induced pain, such as sunburn, or other thermal and nociceptive pain, and chronic pain associated with arthritis. Uses can also include other inflammatory conditions that involve a neurogenic pain-producing component, e.g., certain metastic carcinomas or inflammation of the blood vessels.

For purposes of the subject invention, unless otherwise noted, the terms "inflammation" and "inflammatory response" refer to any and all such inflammatory reactions including, but not limited to, immune-related responses and/or allergic reactions to a physical, chemical, or biological stimulus. "Anti- neurogenic inflammatory activity," as used herein, will be understood by those of ordinary skill in the art to mean biological activity inhibiting or controlling a neurogenic inflammatory response.

The compounds of the subject invention can be used to treat a variety of skin conditions including, but not limited to, radiation irritation and burns (including UV and ionizing), chemical burns, rhinitis, thermal burns, and reddening of the skin.

The compounds of the subject invention can also be used to promote wound healing.

Following are examples which illustrate procedures for practicing the invention. A more complete understanding of the invention can be obtained by reference to the following specific examples of compounds, compositions, and methods of the invention. It will be apparent to those skilled in the art that the examples involve use of materials and reagents that are commercially available from known sources, e.g., chemical supply houses, so no details are given respecting them. These examples should not be construed as limiting. All percentages are by weight and all solvent mixture proportions are by volume unless otherwise noted.

EXAMPLE 1

Preparation of Soritin A, HB-238 (I)

One equivalent of indole was suspended in water and one equivalent of glyoxylic acid was added. The mixture was vigorously stirred at 85° C. for three hours during which a brown precipitate was formed. The precipitate was filtered and dissolved in aqueous NaOH solution (pH=12). Upon acidification (pH=2) with 5 N HCl, the product precipitated and was filtered and dried in vacuum. Yield: 84.5% Characterization: pink crystals, mp: 182° C. (decomposition)

$^1$HNMR($\delta$ DMSO-$d_6$): 12.60 (brs, 1H), 10.96 (2H, s), 7.78 (2H, d,J=8.3), 7.54 (2H, d, J =8.3), 7.43 (2H, s), 7.22 (2H, t, J=7.4), 7.13 (t, 2H, J=7.4), 5.63 (1H, s). $^{13}$CNMR ($\delta$ DMSO-$d_6$): 174.9, 136.7, 126.9, 124.0, 121.4, 119.3, 118.8, 113.2, 111.8, 40.8.

EXAMPLE 2

Synthesis of Bis(3.3'indolyl)methane. HB-236 (II)

Two equivalents of indole was suspended in water and one equivalent of formaldeyde (as formalin) was added. The mixture was vigorously stirred at 85° C. in the dark. After approximately 30 minutes, the product started to precipitate and the reaction mixture was stirred for another five hours. The product was filtered and recrystallized from methanol to yield white crystals. Yield: 79.3%

Characterization: white crystals, mp: 162° C. $^1$H NMR ($\delta$ DMSO-$d_6$): 10.71 (2H, s), 7.53 (2H, d, J=8.0), 7.32 (2H, d, J=8.0),7.14 (2H, s), 7.04 (2H, t, J=7.2), 6.93 (t, 2H, J=7.2), 4.14 (2H, s). $^{13}$C NMR($\delta$ DMSO-$d_6$): 136.4, 127.2, 122.7, 120.7, 118.6, 118.0, 114.2, 111.2, 20.9

EXAMPLE 3

Synthesis of 2,2-Bis(3.3'indolyl) Acetaldehyde. HB-237 (III)

Two equivalents of indole was suspended in water and one equivalent of acetaldehyde dimethyl acetal was added. The mixture was vigorously stirred at 85° C. in the dark. The product started to precipitate and the reaction mixture was stirred for another five hours. The product was filtered and recrystallized from methanol. Yield: 59% Characterization: yellowish crystals, mp: 172° C. $^1$H NMR ($\delta$ DMSO-$d_6$): 10.72 (2H, s), 7.47 (2H, d, J=8.3), 7.34 (2H, d, J=8.3),7.15 (2H, s), 7.03 (2H, t, J=7.4), 6.89 (t, 2H, J=7.4), 4.61 (1H, q, J=7.4), 1.78 (3H, d, J=7.4). $^{13}$C NMR($\delta$ DMSO-$d_6$): 136.8, 126.7, 121.7, 120.8, 120.3, 119.2, 118.0, 111.5, 28.0, 22.1.

EXAMPLE 4

Inhibition of PMA-induced Inflammation (Edema) of the Mouse Ear

The test compound and a known inflammatory agent, phorbol myristate acetate (PMA), are topically applied simultaneously to the left ears of mice. Three hours and 20 minutes following application, the mice are sacrificed. Both left ears and right ears are removed and standard sized bores taken. Edema (inflammation) is measured as the difference in weight between left and right ears (Van Arman, C.G. [1974] Clin. Pharmacol. Ther. 16:900–904.)

Bis-heterocycle compounds of the subject invention, e.g., the bis-indole compounds, show significant antiinflammatory properties. When screened for the ability to reduce edema in mouse ears caused by application of phorbol myristate acetate, soritin A (I) was found to have greater potency than the known anti-inflammatories hydrocortisone, indomethacin, manoalide and topsentin (See Tables 1 and 2).

TABLE 1

Relative potency of soritin A, (I), topsentin, manoalide, hydrocortisone and indomethacin in the topical inhibition of PMA-induced mouse ear edema

| Compound | $ED_{50}$(ug/ear) |
|---|---|
| Hydrocortisone | 20 |
| Indomethacin | 250 |
| Manoalide | 100 |
| Topsentin | 15 |
| Soritin A (I) | 1.3 |

TABLE 2

| Treatment | Right ear (mg) | Left ear (mg) | Difference (mg) | Mean | Standard Dev. | SEM | % Inh. Of Edema |
|---|---|---|---|---|---|---|---|
| PMA | 10 | 23.2 | 13.2 | 13.7 | 0.6 | 0.3 | |
| Control | 9.5 | 22.8 | 13.32 | | | | |
| 2 µg/ear | 8.6 | 23.2 | 14.6 | | | | |
| | 10.1 | 23.6 | 13.5 | | | | |
| Compound I | 10.3 | 12.0 | 1.7 | 1.7 | 0.4 | 0.2 | 87.5 |
| dose: 50 | 10.2 | 11.8 | 1.6 | | | | |
| µgg/ear | 10.5 | 12.7 | 2.2 | | | | |
| | 10.0 | 11.3 | 1.3 | | | | |
| Compound I | 9.9 | 11.6 | 1.7 | 2.1 | 1.3 | 0.7 | 84.9 |
| dose: 25 | 9.9 | 13.3 | 3.4 | | | | |
| µg/ear | 12.5 | 12.9 | 0.4 | | | | |
| | 9.5 | 12.7 | 2.8 | | | | |
| Compound I | 9.5 | 13.6 | 4.1 | 3.1 | 1.9 | 0.9 | 77.3 |
| dose: 12.5 | 8.8 | 10.7 | 1.9 | | | | |
| µg/ear | 9.8 | 11.0 | 1.2 | | | | |
| | 9.7 | 14.9 | 5.2 | | | | |
| Compound I | 10.8 | 12.0 | 1.2 | 3.4 | 2.0 | 1.0 | 75.1 |
| dose: 6.25 | 8.5 | 13.0 | 4.5 | | | | |
| µg/ear | 8.6 | 11.0 | 2.4 | | | | |
| | 9.9 | 15.4 | 5.5 | | | | |
| Compound I | 10.2 | 14.2 | 4.0 | 6.4 | 2.6 | 1.3 | 52.9 |
| dose: 3.12 | 9.0 | 17.7 | 8.7 | | | | |
| µg/ear | 9.2 | 17.9 | 8.7 | | | | |
| | 8.6 | 12.9 | 4.3 | | | | |

EXAMPLE 5

Inhibition of Resiniferatoxin-induced Inflammation (Edema) of the Mouse Ear

Induction of mouse ear edema can be conducted according to known methods (Inoue, 1-f., N. Nagata, Y. Koshffiara [1993]). Compounds to be tested for anti-neurogenic inflammatory activity are topically applied in acetone to the ears of mice in a solution that includes the edema-causing irritant resiniferatoxin (RTX). RTX alone (0.1 µg/ear) or in combination with various dilutions of test compound are applied to both sides of the left ears (5 mice per treatment group) and acetone is applied to all right ears. After a 30-minute incubation, the mice are sacrificed, the ears removed, and bores taken and weighed. Edema is measured by subtracting the weight of the right ear (acetone control) from the weight of the left ear (treated). Results are recorded as % decrease (inhibition) or % increase (potentiation) in edema relative to the control group edema.

Soritin A proved to be capable of reducing edema in mouse ears caused by application of resiniferatoxin (RTX). At a dose of 50 μg/ear of soritin A (I), RTX-induced edema was inhibited by approximately 97.7%. The $ED_{50}$ for inhibition of RTX-induced edema was observed to be 5.1 μg/ear (Table 3).

TABLE 3

| Treatment | Right ear (mg) | Left ear (mg) | Difference (mg) | Mean | Standard Dev. | SEM | % Inh. Of Edema |
|---|---|---|---|---|---|---|---|
| RTX | 10.2 | 20.2 | 10.0 | 12.0 | 2.2 | 1.0 | |
| Control | 10.5 | 23.7 | 13.2 | | | | |
| 0.1 μg/ear | 10.3 | 24.4 | 14.1 | | | | |
| | 10.9 | 24.4 | 13.5 | | | | |
| | 11.2 | 20.5 | 9.3 | | | | |
| Compound I | 9.9 | 14.0 | 4.1 | 1.5 | 1.7 | 0.7 | 87.9 |
| 25 μg/ear | 9.7 | 9.9 | 0.2 | | | | |
| | 10.0 | 12.1 | 2.1 | | | | |
| | 11.7 | 12.3 | 0.6 | | | | |
| | 10.6 | 10.9 | 0.3 | | | | |
| Compound I | 12.1 | 15.9 | 3.8 | 2.8 | 1.1 | 0.5 | 76.8 |
| 12.5 μg/ear | 10.6 | 14.2 | 3.6 | | | | |
| | 10.7 | 13.8 | 3.1 | | | | |
| | 10.7 | 11.8 | 1.1 | | | | |
| | 10.9 | 12.6 | 1.7 | | | | |
| | 11.1 | 14.5 | 3.4 | | | | |
| Compound I | 11.2 | 17.2 | 6.0 | 8.0 | 2.4 | 1.0 | 33.6 |
| 6.25 μg/ear | 11.9 | 23.1 | 11.2 | | | | |
| | 11.8 | 19.1 | 7.3 | | | | |
| | 10.6 | 20.7 | 10.1 | | | | |
| | 12.6 | 20.9 | 8.3 | | | | |
| | 11.8 | 16.8 | 5.0 | | | | |
| Compound I | 12.2 | 18.2 | 6.0 | 6.0 | 1.0 | 0.4 | 49.9 |
| 3.12 μg/ear | 10.8 | 16.8 | 6.0 | | | | |
| | 10.6 | 17.2 | 6.6 | | | | |
| | 12.6 | 19.7 | 7.1 | | | | |
| | 12.0 | 16.1 | 4.1 | | | | |
| | 11.8 | 18.1 | 6.3 | | | | |

In addition, the bis-indole compounds Bis(3,3'indolyl)methane (II) and 2,2-Bis (3,3'indolyl) acetaldehyde (III) were tested for percent inhibition of RTX-induced edema. These compounds also show activity in this assay (Table 4).

TABLE 4

Percent inhibition of RTX-induced edema in mouse ears by soritin A and analogs

| | Compound Name | Dose | % Inhibition of edema |
|---|---|---|---|
| Soritin A | HB-238 | 50 μg/ear | 97.7 |
| Bis(3,3'indolyl)methane | HB-236 | 50 μg/ear | 59.1 |
| Bis(3,3'indolyl)acetaldehyde | HB-237 | 50 μg/ear | 50.1 |

EXAMPLE 6

Formulation and Administration

The compounds of the invention are useful for various non-therapeutic and therapeutic purposes. It is apparent from the testing that the compounds of the invention are effective for anti-inflammatory uses.

Therapeutic application of the new compounds and compositions containing them can be contemplated to be accomplished by any suitable therapeutic method and technique presently or prospectively known to those skilled in the art. Further the compounds of the invention have use as starting material for intermediates for the preparation of other useful compounds and compositions.

In one preferred embodiment, the compounds or compositions of the subject invention are administered in a lotion or other cosmetic preparation. This administration is done directly to the skin where anti-inflammatory activity is desired.

The dosage administration to a host in the above indications will be dependent upon the identity of the condition to be treated, the type of host involved, its age, weight, health, kind of concurrent treatment, if any, frequency of treatment, and therapeutic ration.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

Typically, the compositions of the subject invention will be formulated and packaged in a manner particularly adapted for use as an anti-inflammatory agent. Thus, such compositions would typically be accompanied with labeling or other literature describing the use of the composition as an anti-inflammatory agent.

In accordance with the invention, pharmaceutical compositions comprising, as active ingredient, an effective amount of one or more of the subject compounds and one or more non-toxic, pharmaceutically acceptable carriers or diluents can be used by persons of ordinary skill in the art. In addition, the pharmaceutical composition can comprise one or more of the bis-heterocycle compounds, e.g., a bis-indole, as a first active ingredient plus a second active ingredient comprising an anti-inflammatory compound known in the art. Such known anti-inflammatory drugs include, but are not limited to, the steroidal anti-inflammatory drugs and the non-steroidal anti-inflammatory drugs (NSAIDs).

In accordance with this invention, pharmaceutically effective amounts of a known anti-inflammatory agent and the bis-heterocycle compounds are administered sequentially or concurrently to the patient. The most effective mode of administration and dosage regimen of bis-heterocycle compounds and anti-inflammatory agent will depend upon the type of condition to be treated, the severity and course of that condition, previous therapy, the patient's health status, and response to bis-indoles and the judgment of the treating physician. Bis-heterocycle compositions may be administered to the patient at one time or over a series of treatments.

Preferably, the bis-heterocycle, e.g., a bis-indole composition, and any second anti-inflammatory agent are administered sequentially to the patient, with the anti-inflammatory agent being administered before, after, or both before and after treatment with the bis-indole compound. Sequential administration involves treatment with the anti-inflammatory agent at least on the same day (within 24 hours) of treatment with bis-indole and may involve continued treatment with the anti-inflammatory agent on days that the bis-indole is not administered. Conventional modes of administration and standard dosage regimens of anti-inflammatory agents may be used (see Gilman, A. G. et. al. [eds] *The Pharmacological Basis of Therapeutics*, pp. 697–713, 1482, 1489–1491 [1980]; Physicians Desk Reference, 1985 Edition). For example, indomethacin can be administered orally at a dosage of about 25–50 mg, three times a day. Higher doses can also be used. Alternatively, aspirin (about 1500–2000 mg/day), ibuprofen (about 1200–3200 mg/day), or conventional therapeutic doses of other anti-inflammatory agents can be used. Dosages of anti-inflammatory agents can be titrated to the individual patient.

According to one embodiment of this invention, the patient may receive concurrent treatments with the anti-inflammatory agents and compositions comprising bis-heterocycles, e.g. bis-indoles. For example, local intralesional, or intravenous injection of bis-indoles is preferred (see Gilman et. al supra at pp. 1290–91). The anti-inflammatory agent should preferably be administered by subcutaneous injection, subcutaneous slow release implant, or orally.

Alternatively, the patient can receive a composition comprising a combination of one or more bis-indole compounds and an anti-inflammatory agent according to conventional modes of administration of agents which exhibit antibacterial, anticancer, antitumor or anti-inflammatory activity. These include, for example, parenteral, subcutaneous, intravenous, or intralesional routes of administration.

The compounds used in these therapies can also be in a variety of forms. These include for example, solid, semi-solid and liquid dosage forms, such as tablets, pills, powders, liquid solutions or suspensions, suppositories, injectable and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

The compounds of the subject invention may also be administered utilizing liposome technology, slow release capsules, implantable pumps, and biodegradable containers. These delivery methods can, advantageously, provide a uniform dosage over an extended period of time.

Examples of such carriers or diluents include ethanol, dimethyl sulfoxide, glycerol, silica, alumina, starch and equivalent carriers and diluents. While effective amounts may vary, as conditions in which compositions are used vary, a minimal dosage required for anti-inflammatory activity is generally between 0.01 and 100 μg of the compound. To provide for the administration of such dosages for the desired therapeutic treatment, new pharmaceutical compositions of the invention will advantageously comprise between about 0.1% and 45%, and especially m, 1 and 15% by weight of the total of one or more of the new compounds based on the weight of the total composition including carrier or diluent.

Illustratively, dosage levels of the administered active ingredients can be: intravenous, 0.01 to about 50 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg and preferably about 1 to 100 mg/kg; intranasal instillation, 0.01 to about 50 mg/kg; and aerosol, 0.01 to about 50 mg/kg of animal (body) weight.

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

It should be understood that the examples and embodiments described herein are of illustrative purposes only and that various modification or changes in light thereof will be suggested to persons skilled in the art and are to be included within the spirit and purview of this application and the scope of the appended claims.

What is claimed is:

1. A method of treating inflammation in a human or animal, wherein said method comprises administering to said human or animal an effective amount of a compound having the following structure:

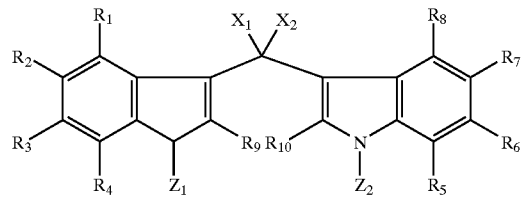

wherein $R_{1-10}$ are the same or different and are selected from the group consisting of —H, —OH, halogen, —COOH, —COOR, C1–C8 alkyl, C1–C8 alkoxyl, mesyl, tosyl, —OCOR, and $NZ_1Z_2$ (wherein the Zs can be the same or different);

$X_1$ and $X_2$ are the same or different and are selected from the group consisting of —H, —R, —COY, and $C(NZ_1)Y$;

Y is —H, —OH, $NZ_1Z_2$ (wherein the $Z_1$ and $Z_2$ can be the same or different) C1–C8 alkyl, C1–C8 alkoxyl or an amino acid linked through the amine functionality forming an amide bond;

$Z_1$ and $Z_2$ are the same or different and are selected from the group consisting of —H, —OH, C1–C8 alkyl, C1–C8 alkoxyl and —COR; and R is C1–C8 alkyl, or aryl.

2. The method, according to claim 1, wherein $X_1$=H, $X_2$=COOH, $R_1$-$R_{10}$=H and $Z_1$, $Z_2$=H.

3. The method, according to claim 1, wherein $X_1$=$X_2$=H, $R_1$-$R_{10}$ are H, and $Z_1$=$Z_2$=H.

4. The method, according to claim 1, wherein $X_1$=H, $X_2$=$CH_3$, $R_1$-$R_{10}$ are H and $Z_1$=$Z_2$=H.

5. The method, according to claim 1, wherein said method is used to treat inflammation of immunogenic origin.

6. A method for treating an inflammatory condition, in a human or animal, wherein said condition is selected from the group consisting of pain; burns; allergic responses; rheumatoid arthritis; osteoarthritis; other inflammatory conditions involving acute joint inflammation, chronic joint inflammation, or both; wound healing; anaphylactic reactions; inflammatory bowel disease; nephritis; conjunctivitis; inflammatory gum disease; acute asthmatic attack and inflammation of the lung due to chemical exposure, said method comprising administering an effective amount of a bis-heterocyclic compound or a salt, analog, or derivative thereof, wherein said compound has the following structure:

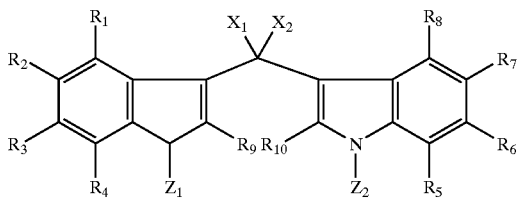

wherein $R_{1-10}$ are the same or different and are selected from the group consisting of —H, —OH, halogen, —COOH, —COOR, C1–C8 alkyl, C1–C8 alkoxyl, mesyl, tosyl, —OCOR, and $NZ_1Z_2$ (wherein the Zs can be the same or different);

$X_1$ and $X_2$ are the same or different and are selected from the group consisting of —H, —R, —COY, and $C(NZ_1)$ Y;

Y is —H, —OH, $NZ_1Z_2$ (wherein the $Z_1$ and $Z_2$ can be the same or different) C1–C8 alkyl, C1–C8 alkoxyl or an amino acid linked through the amine functionality forming an amide bond;

$Z_1$ and $Z_2$ are the same or different and are selected from the group consisting of —H, —OH, C1–C8 alkyl, C1–C8 alkoxyl and —COR; and R is C1–C8 alkyl, or aryl.

7. The method, according to claim 6, wherein said pain is caused by a condition selected from the group consisting of migraine, rhinitis, thermal induced pain, radiation induced pain, and chemical induced pain.

8. The method, according to claim 6, wherein said burn is selected from the group consisting of chemical burns, chemical induced lesions, radiation burns, and thermal burns.

9. The method, according to claim 6, wherein said condition is allergic response.

10. The method, according to claim 6, wherein said treatment facilitates the promotion of wound healing.

11. The method, according to claim 6, wherein said condition is a systemic anaphylactic reaction in an animal or a human.

12. The method, according to claim 6, wherein said condition is inflammatory bowel disease.

13. The method, according to claim 6, wherein said condition is nephritis.

14. The method, according to claim 6, wherein said condition is conjunctivitis.

15. The method, according to claim 6, wherein said condition is inflammatory gum disease.

16. The method, according to claim 6, wherein said condition is selected from the group consisting of acute asthmatic attack and inflammation of the lung from chemical exposure.

17. The method, according to claim 6, wherein said condition is selected from the group consisting of rheumatoid arthritis, osteoarthritis, and other inflammatory conditions involving acute joint inflammation, chronic joint inflammation, or both.

* * * * *

UNITED STATES PATENT AND TRADEMARK OFFICE
CERTIFICATE OF CORRECTION

PATENT NO. : 6,444,697 B2  Page 1 of 1
DATED : September 3, 2002
INVENTOR(S) : Amy E. Wright, Ralph-Heiko Mattern and Robert S. Jacobs It is certified that error appears in the above-identified patent and that said Letters Patent is hereby corrected as shown below:

Column 4,
Line 23, "inflammation. Neurogenic" should read as two paragraphs -- inflammation. Neurogenic --.

Column 5,
Line 28, "7.78 (2H, d,J=8.3)" should read -- 7.78 (2H, d, J=8.3)" --.
Line 34, "(3.3'indolyl)methane." should read -- (3,3'indolyl)methane, --.
Line 44, "J=8.0),7.14" should read -- J=8.0), 7.14 --.
Line 49, "(3.3'indolyl) Acetaldehyde." should read -- (3,3'indolyl) acetaldehyde,--.

Column 6,
Line 17, "A. (I)." should read -- A, (I), --.
Line 40, "$\mu$gg/ear" should read -- $\mu$g/ear --.

Column 10,
Line 67, "bums" should read -- burns --.

Column 12,
Line 5, "bum" should read -- burn --.
Lines 7-8 ,"radiation bums, and thermal bums." should read -- radiation burns, and thermal burns. --.

Signed and Sealed this

First Day of April, 2003

JAMES E. ROGAN
*Director of the United States Patent and Trademark Office*